United States Patent [19]

Madison

[11] Patent Number: 5,517,998
[45] Date of Patent: May 21, 1996

[54] CLOSED LOOP PRESSURE DETERMINATION SYSTEM AND METHOD FOR FIBER OPTIC PRESSURE TRANSDUCER SYSTEM

[75] Inventor: Dennis S. Madison, Ramsey, Minn.

[73] Assignee: MedAmicus, Inc., Minneapolis, Minn.

[21] Appl. No.: 186,007

[22] Filed: Jan. 24, 1994

[51] Int. Cl.$^6$ ........................................ A61B 5/02
[52] U.S. Cl. ........................ 128/667; 128/675; 128/748
[58] Field of Search ........................... 128/748, 667, 128/673, 666, 675

[56] References Cited

U.S. PATENT DOCUMENTS

| | | | |
|---|---|---|---|
| 3,686,958 | 8/1972 | Porter et al. | 73/406 |
| 3,703,099 | 11/1972 | Rouse | 73/398 |
| 3,789,667 | 2/1974 | Porter et al. | 73/406 |
| 4,210,029 | 7/1980 | Porter | 73/705 |
| 4,342,218 | 8/1982 | Fox | 73/4 |
| 4,672,974 | 6/1987 | Lee | 128/673 |
| 4,779,626 | 10/1988 | Peel et al. | 128/675 |
| 4,901,735 | 2/1990 | von Berg | 128/748 |
| 4,936,310 | 6/1990 | Engstrom et al. | 128/673 |
| 5,005,584 | 4/1991 | Little | 128/748 |
| 5,313,957 | 5/1994 | Little | 128/675 |

OTHER PUBLICATIONS

Levin, "The Use of a Fiberoptic Intracranial Pressure Monitor in Clinical Practice," in *Neurosurgery*, vol. 1, pp. 266–271, 1977.

Wald et al., "A new technique for monitoring epidural intracranial pressure," Medical Instrumentation, vol. 11, pp. 352–354, 1977.

*Primary Examiner*—Angela D. Sykes
*Assistant Examiner*—Eric F. Winakur
*Attorney, Agent, or Firm*—Moore & Hansen

[57] ABSTRACT

A closed loop control system for a fiber optic pressure transducer and a method of operation for such a system are disclosed. A flexible, pressure sensitive membrane of the pressure transducer is pressure coupled on one surface to a pressure to be measured and on its opposite surface to a sealed passage within an optical fiber pathway connected to a control module. The pressure within the passage is adjusted by a pressure generator to compensate for changes in the pressure being measured, in response to an output signal from a comparator in the control module. That output signal is the result of a comparison between a predetermined reference pressure signal and a modulated light signal from the pressure transducer indicative of a change in the measured pressure. The adjusted pressure within the lumen passage is sensed to provide a pressure reading equivalent to the measured pressure, since the pressure in the lumen passage is adjusted to equalize the pressures on the opposite surfaces of the pressure sensitive membrane.

7 Claims, 2 Drawing Sheets

CLOSED LOOP PRESSURE DETERMINATION SYSTEM AND METHOD FOR FIBER OPTIC PRESSURE TRANSDUCER SYSTEM

The present invention relates generally to control systems for pressure transducers of the optical fiber type and particularly to such systems that utilize a closed loop system and method of determining a pressure of interest.

BACKGROUND OF THE PRESENT INVENTION

Pressure transducers of the optical fiber type, commonly known as fiber optic pressure transducers, are becoming well known and, consequently, widely used, for and because of their ability to accurately sense pressure changes in specialized environments. In particular, the medical community is taking advantage of the sensitivity and quick response provided by these devices by using them to measure pressures within, for example, the blood system, the lungs, the urinary tract, and the cranial cavity.

Typically, these devices include a pressure responsive member having a first surface exposed to the pressure desired to be measured and a second surface exposed to ambient atmospheric pressure. The devices usually also include a housing that holds the pressure responsive member in a predisposed position relative to a housing aperture that allows the pressure responsive member to flex in the direction of least pressure in response to changing pressures. The housing also holds the distal end of an optical pathway in a predetermined position relative to the housing aperture and the pressure responsive member. The optical pathway includes a transmission path and a return path. Light is sent through the pathway on the transmission path from its proximal end to its distal end and then back through the pathway on the return path. Pressure deviations across the two surfaces of the pressure responsive member result in the movement of the pressure responsive member into and out of the path of the light travelling along the pathway, thereby modulating the return light signal by variably obstructing the light signal. This modulation of the light signal results in changes in the intensity of the light returning through the pathway. A control unit receives the returned light signal and then, after appropriate conditioning of the return signal, compares the intensity of the returning light signal with a correlation scheme that has been previously established between the measured intensity of the returned light signal and the pressure sensed by the pressure responsive member. This correlation scheme then provides an indication of the sensed pressure. Often, the pathway will include a reflector disposed at the distal end of the optical pathway in an optical coupling relation between the light transmission path and the light return path.

These fiber optic transducer devices can be made quite small and from biocompatible materials, thereby making their use with patients relatively comfortable as well as safe. Furthermore, they provide the attending clinician or physician with accurate, rapid responses indicative of pressure changes within the patient's system. These rapid responses are particularly advantageous where used with rapidly changing pressures.

Presently, most of these devices rely, as noted, upon a control unit that compares the sensed pressure, that is, the measured intensity of the returning light signal, with a previously established correlation between a particular light intensity and a measured pressure. A calibration cycle is run before first use so as to generate a correlation profile between later measured light intensities and known measured pressures. With these devices, the accuracy of the pressure measurement is completely dependent upon the accuracy of the predetermined correlation scheme established during the calibration sequence. This accuracy is in turn dependent upon the elasticity of the pressure responsive member. The deflection of the pressure responsive member is a function of the pressure differential experienced by the member divided by the member's elasticity constant. Thus, any change in the elasticity of the member during use will result in a change in the deflection and the modulation of the light beam, leading to pressure readings derived from the previously established correlation profile that deviate from the true pressure. Another problem with such correlation schemes is that they must cover a range of possible sensed pressures, and it is more likely that errors may occur in the correlation scheme at the pressure extremes. In addition, since the correlation scheme is established for ambient atmospheric pressure at the time the calibration sequence is run, it should be corrected as the ambient pressure changes or false readings of the sensed pressure may result. While not a great problem normally, situations do arise where rapid changes in atmospheric pressure do occur, especially when viewed within the time frame of a continuous monitoring of a patient.

Another concern of the foregoing known type of fiber optic pressure transducers is that construction of the transducer apparatus itself must be kept within critical parameters since the measured intensity of the returning light signal determines the sensed pressure. Thus, transducer construction becomes critical since the returning light signal must be linear and of a particular magnitude dependent upon the apparatus. Because a linear signal is needed, the foregoing known systems of calibration and control also require the use of linearization software on the returning light signal.

It would be desirable therefore to have a fiber optic pressure transducer that was less susceptible to errors creeping into the pressure measurement process due to inherent limitations in the pressure responsive member itself as well as the calibration system used to establish the correlation profile between the returning light signal intensity and the measured, that is, sensed, pressure.

SUMMARY OF THE PRESENT INVENTION

It is an object of the present invention to provide a new and improved method of determining a pressure within a particular environment using a fiber optic pressure transducer that is not subject to the foregoing disadvantages.

It is another object of the present invention to provide a method for determining a pressure within a particular environment by utilizing a closed loop control system.

It is still another object of the present invention to provide a method for determining a pressure within a particular environment that compares the intensity of a returned light signal with a reference signal and consequently adjusts the pressure within a sealed lumen to equalize the signals and, therefore, the pressures internal and external of a fiber optic pressure transducer, and to provide an indication of the pressure within the particular environment.

It is yet another object of the present invention to provide a system for determining pressure that has a sealed lumen passage pressure coupled to a surface of a pressure responsive member, the opposing surface of the pressure responsive member being pressure coupled to the pressure sought to be determined, that utilizes a pressure controller to equalize the pressure exerted on the opposing surfaces of the pressure responsive member, and that utilizes a reference pressure transducer to measure the pressure within the sealed lumen passage, thereby providing an indication of the pressure sought to be determined.

The foregoing objects of the present invention are provided by a closed loop control system for a fiber optic pressure transducer and a method of operation of a closed loop control fiber optic system. A system in accord with the present invention has an optical fiber pathway extending between a control module and a pressure transducer of the optical fiber type. The optical fiber provides a light path for a light signal to and from the pressure transducer. The optical pathway is contained within a transducer lumen that also includes a passage sealed to the external environment. The passage is pressure coupled to one surface of a pressure responsive member so as to be exposed to a pressure $p_2$, the other surface of the member being exposed to the pressure $p_1$ sought to be measured. The proximal end of the transducer lumen is connected to a chamber whose pressure, and thus the pressure within the lumen and $p_2$, is controlled by a pressure variation means, all of which may be disposed within the control module. A precalibrated reference transducer is also connected to the pressure chamber to provide an output signal indicative of the pressure within the pressure chamber and, therefore, $p_2$. The pressure variation means changes the pressure within the lumen in response to a signal provided by a comparator that compares a reference signal indicative of a pressure $p_{ref}$ and the output signal from the fiber optic transducer (after appropriate signal conditioning well known to the art).

The reference signal is established prior to use for a condition where, preferably, $$p_1-p_2=\Delta p=0,$$

that is, typically where $p_1=p_2$=ambient air pressure. Under this condition the output signal from the transducer indicates that the pressure on both the inner and outer surfaces of the pressure responsive member are equal. Thus, at the zeroing stage prior to use of the present invention, when $p_1=p_2$, then $p_{ref}=p_1=p_2$=ambient air pressure. During use of the present invention, when the pressures vary from equality, that is, when $\Delta p \neq 0$, the comparator generates a signal that drives the pressure variation means so as to change the pressure internally of the lumen and thus on the second surface of the pressure responsive member so as to equalize the pressure across the pressure responsive member and to keep $\Delta p=0$. Thus, because $p_1=p_2$, measuring $p_2$ with the reference transducer provides a signal indicative of $p_1$.

Stated again, the present invention provides a means for equalizing the pressure differential experienced by opposing, that is the obverse and reverse, surfaces of a pressure responsive member and a means for determining the pressure on one of the surfaces, such as the obverse surface, thereby providing a determination of the pressure on the other, or reverse, surface. Apparatus in accord with the present invention obviates the need for the previously referred to pre-use calibration of the system, thereby reducing the number of potential error sources in measuring the pressure, and also reduces the criticality of transducer construction and the elasticity of the pressure responsive member to accurate pressure readings.

The foregoing objects of the invention will become apparent to those skilled in the art when the following detailed description of the invention is read in conjunction with the accompanying drawings and claims. Throughout the drawings, like numerals refer to similar or identical parts.

DETAILED DESCRIPTION OF THE PRESENT INVENTION

Figure 1:
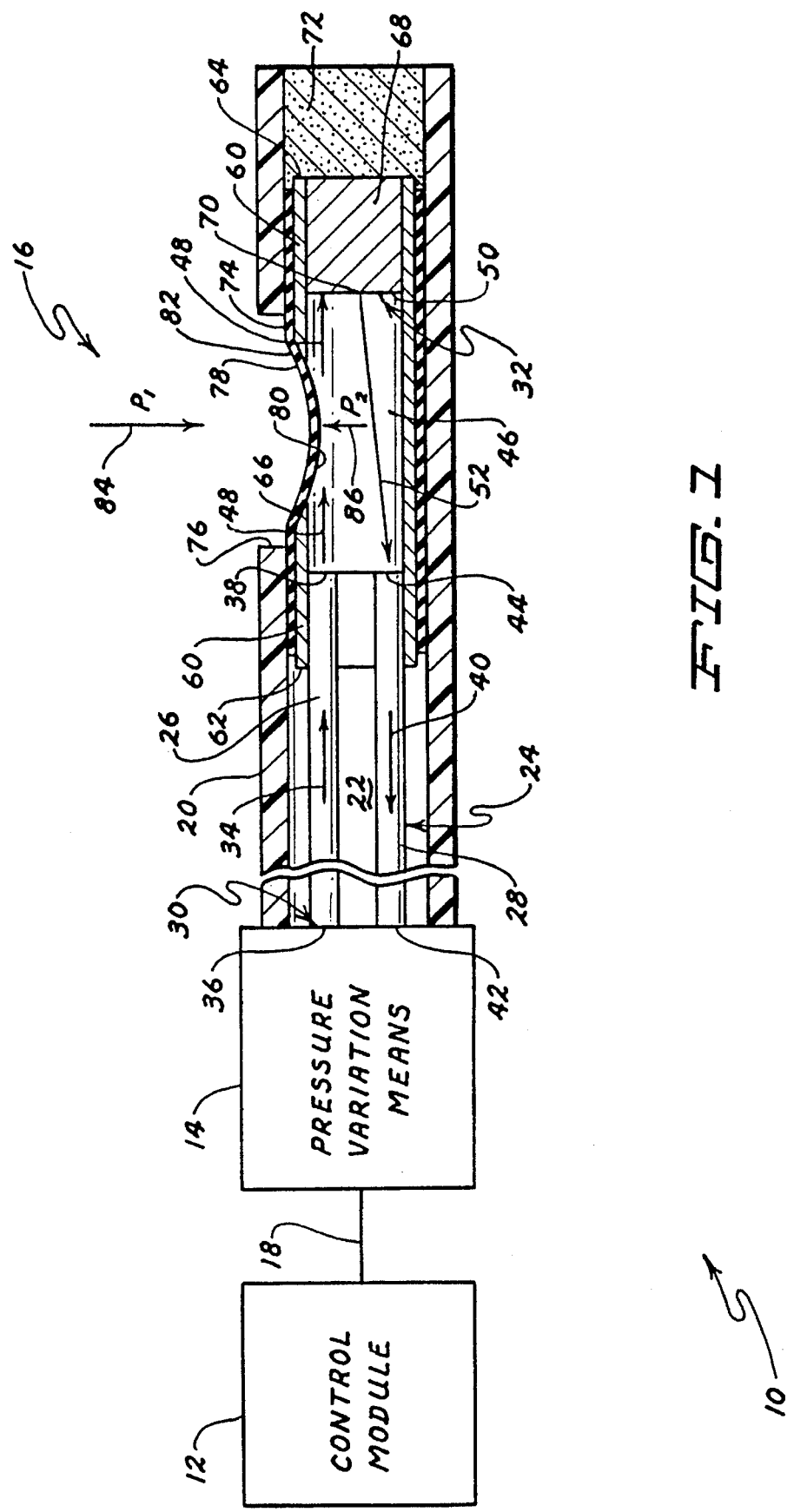
FIG. 1 shows a closed loop fiber optic pressure transducer system, partially in cross section in accord with the present invention.

FIG. 1 shows a closed loop fiber optic pressure transducer system 10 in accord with the present invention. System 10 includes a control module 12, a pressure variation means, or generator, 14, and a fiber optic pressure transducer apparatus 16. As is well known in the art, control module 12 comprises a light generator (not shown) for producing light signals that travel through the transducer apparatus 16, and an appropriate microprocessor (not shown) that controls the operation of pressure variation means 14, as will be discussed further below. The microprocessor controls the operation of pressure variation means 14 through the appropriate programming over an appropriate connection 18 based upon pressure sensed by a pressure transducer apparatus 16 to be described below.

Pressure transducer apparatus 16 is sealed generally to the outside environment. Pressure transducer apparatus 16 includes a lumen 20 having at least one interior passage 22 that is sealed to the outside ambient atmosphere by well known means. Apparatus 16 further includes an optical pathway 24 that may comprise a single optical fiber, a pair of optical fibers 26 and 28 as shown, or an optical fiber bunch as is well known to the art. Optical pathway 24 may be disposed within sealed passage 22 as shown, or, if desired, a separate passage within lumen 20 may be utilized for the optical pathway 24. Optical pathway 24 has a proximal end 30 and a distal end 32. Each fiber, in turn, also has proximal and distal ends. Thus fiber 26, which serves partially as the transmission path from the proximal end 30 to the distal end 32 of the optical pathway, as indicated by arrow 34, has a proximal end 36 and a distal end 38. Similarly, fiber 28, which serves partially as the return path from the distal end 32 to the proximal end 30 of the optical pathway, as indicated by arrow 40, has a proximal end 42 and a distal end 44. Light signals, typically of the type produced by a light emitting diode (LED) are transmitted from the proximal end 30 of pathway 24 disposed generally within control module 12 through the optical pathway 24 to the distal end 32 of the pathway 24 and then back to the control module. Thus, as seen in FIG. 1, light travels from control module 12 through fiber 26 to its distal end 38, across a gap 46 as indicated by arrows 48 to a reflector 50, which serves as the distal end 32 of pathway 24. The light signal is reflected by reflector 50 back across gap 46 to the distal end 44 of fiber 28 as indicated by arrow 52.

The distal end 32 of pathway 24 may terminate in a housing 60. Housing 60 typically has a substantially hollow cylindrical configuration, has proximal and distal ends 62 and 64, respectively, and includes an aperture 66 in the wall thereto. Thus, the distal end 32 of pathway 24 is received within the bore of housing 60 at the proximal end 62 thereof. The distal end 64 of housing 60 receives an end plug 68.

Reflector 50 may comprise a reflective surface disposed on the proximal end 70 of end plug 68. Housing 60 may be affixed in place within lumen 20 by an appropriate adhesive or potting material 72, as is well known in the art.

A pressure responsive member 74 is disposed in coveting relation to housing aperture 66 and the housing 60 and accompanying pressure responsive member 74 are disposed within lumen 20 closely adjacent a wall opening 76 therein. Pressure responsive member 74 is disposed such that a first or outer surface 78 is exposed, that is, pressure coupled, to the pressure sought to be determined, such as an intracranial pressure, by means of wall opening 76, and a second or interior surface 80 is exposed, that is, pressure coupled, to the pressure within lumen passage 22. Where a separate passage is used for the optical pathway 24, as noted earlier, the sealed lumen passage would still be pressure coupled to surface 80.

Pressure responsive member 74 is disposed on housing 60 for the purpose of sensing the pressure and changes in the pressure of the particular environment in which the member 74 is disposed. Member 74 may take the form of a patch or, as shown, a sleeve that completely and snugly encircles housing 60. Member 74 flexes either inwardly or outwardly as the pressure on surface 78 changes. It is understood that "inward" refers to a direction towards the center of the housing 60. The portion of flexible member 74 that overlies the aperture 66 in the housing 60 is a pressure-sensitive segment 82, which is free to flex or deflect transversely with respect to the path of light passing longitudinally between the distal end 32 of optical pathway 24 and reflector 50. The material of the membrane sleeve is preferably elastomeric, and could be urethane or silicone. In addition, it is also known in the art to use membranes made of a metallic material. These metallic membranes may also be used with the present invention.

As a particularly beneficial feature, the pressure responsive member 74 is secured around the outside of housing 60 over the aperture 66 cut therein so as to be placed in tension in a prestressed condition. Pre-stressing in tension member 74 around housing 60 and over the aperture 66 causes the member to be initially set at an inwardly flexed condition in which pressure responsive segment 82 thereof is curved inwardly. The pressure responsive member 74 is placed in tension a predetermined extent so that segment 82 will have an inward, sufficient deflection so that segment 82 will extend slightly into the linear path of light traveling between distal end 38 of light transmission fiber 26 and reflector 50. Segment 82 is free to flex either inwardly or outwardly. Thus, because of its initial, inward deflection partially blocking the flow of light through the fiber optic light-transmitting circuit and because passage 22, which is pressure coupled to the second or interior surface 80 of flexible segment 82, will be at ambient atmospheric pressure when the apparatus 10 is zeroed, as described earlier, segment 82 is able to sense negative pressures or pressures below atmospheric pressure within the body of a patient. Thus, if the pressure being sensed externally of pressure responsive member 74 decreases, the segment 82 will flex slightly outwardly to permit a greater passage of light between the distal end 32 of pathway 24 and reflector 50. The deflection of segment 82 in response to changes in the pressure differential across its inner and outer surfaces is assured by coupling the inner surface 80 of segment 82 to the pressure within passage 22, which is sealed to the outside atmosphere.

Changes in light transmission will be sensed as a signal indicating a change in pressure, either positive or negative, that is, an increase or decrease, on the first or exterior surface. The returned, pressure responsive member modulated light signal will be appropriately conditioned and then will be compared with a preestablished signal $p_{ref}$ indicative of a condition where $p_1$, as indicated by arrow 84, the pressure on the member first surface 78, is equal to $p_2$, the pressure on the second surface 80, as indicated by arrow 86. That is, the reference signal $p_{ref}$ will be established for a $p_1=p_2$ condition. Normally, this zeroing of the apparatus 10 will occur before first use and where $p_1$ is equal to ambient atmospheric pressure. Thus, sealed lumen passage 22 will be exposed to ambient atmospheric pressure while pressure transducer and, in particular, first or outer surface 78 of pressure responsive member 74 are also so exposed, and a light signal will be sent through optical pathway 24 to establish the reference signal $p_{ref}$. In operation, the control module 12, as noted will compare the modulated light signal returned from the distal end 32 of the optical pathway 24, which is indicative of the pressure difference across the pressure responsive member 74, that is, $p_1-p_2$, with the preestablished reference signal $p_{ref}$ and will send an output signal equal to $\Delta p = p_{ref} - (p_1 - p_2)$ to the pressure variation means 14 to change the pressure within the lumen passage 22 accordingly until the returned light signal and the preestablished reference signal are equal, thereby indicating that the pressure on the first and second, or the exterior and inner surfaces 78, 80 respectively of pressure responsive segment 82 are equal. A reference transducer, which may be of any well known type or manufacture, can then be referred to for a reading of what the pressure $p_2$, and, therefore, $p_1$ since $p_2=p_1$, is.

Figure 2:
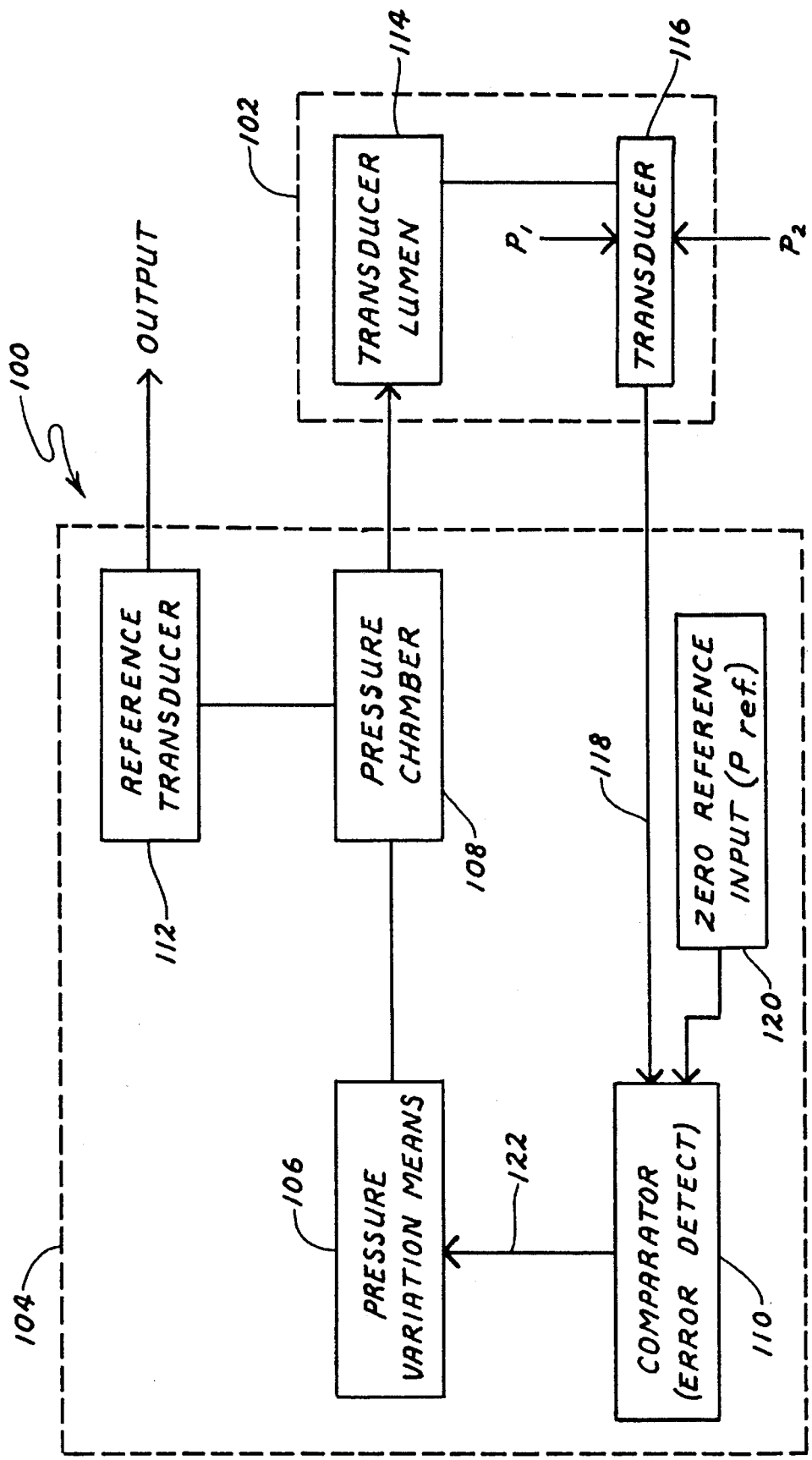
FIG. 2 illustrates in a schematic view a pressure transducer and a closed loop control system as shown in FIG. 1 and in accord with the present invention.

FIG. 2 shows in greater detail a schematic view of an apparatus and system in accord with the present invention. Thus, FIG. 2 shows a closed loop control system 100 and its associated transducer apparatus 102. Apparatus 100 includes a control unit 104 that includes a pressure variation means 106, a pressure chamber 108, a comparator 110, and a reference transducer 112. The transducer apparatus 102 includes a transducer lumen 114, similar or identical to the aforementioned lumen 20, and a pressure transducer 116.

As shown in the Figure, transducer 116 provides an output signal, which is the modulated light signal previously discussed, to the comparator 110 via a connection 118 comprising an optical pathway such as pathway 24. Comparator 110 compares the transducer output signal with a preestablished reference signal 120 and provides a comparator output signal to the pressure variation means 106 via a connection 122. Pressure variation means 106 in turn increases or decreases the pressure within pressure chamber 108, which is pressure coupled to sealed transducer lumen 114, thus restoring the pressure within lumen 114 and on the interior of transducer to equality. The reference transducer 112, which is pressure coupled to the pressure chamber 108 will then serve as a pressure sensing device to read off the pressure inside the pressure chamber, which, since reference transducer 112 is coupled to lumen 114 will be the same as the pressure $p_2$, will provide an indication of the pressure $p_1$.

In operation, the pressure transducer would be zeroed at atmospheric pressure prior to use to establish the reference signal for a pressure difference $\Delta p=0$, that is, for a condition where $\Delta p = p_1 - p_2 = 0$. This reference pressure signal $p_{ref}$ will be supplied to one side of the comparator 110 during operation while the other side of the comparator 110 will be supplied with the appropriately conditioned signal from the transducer 116. This transducer 116 output signal will be indicative of the change in the pressure, that is the pressure difference across the pressure responsive member, $p_1-p_2$.

The output of the comparator 110 will be supplied to pressure variation means 106, which may, for example, comprise a speaker coil similar to that used in audio applications. Since such devices are well known to the art, further elucidation is deemed unnecessary. Movement of the diaphragm of such a speaker coil will result in changes in pressure within passage 22 as desired. In such a circumstance, the pressure variation means 106 and pressure chamber 108 can essentially be a unitary structure.

After zeroing the transducer 116, it can be emplaced in the desired environment, such as the cranial cavity of a human being. As the pressure changes on the exterior surface of the transducer creating a $\Delta p = p_1 - p_2 \neq 0$ condition, the pressure responsive member of the transducer 116 will deflect accordingly, changing the intensity of the light signal returned from the distal end of the optical pathway. This returned signal will create an error condition in the comparator 110 (error detect) which in turn will provide an output to the pressure variation means 106 to vary the pressure $p_2$ within the lumen 114 such that $\Delta p$ along with the error signal returns to zero; that is, such that a $p_1 = p_2$ condition is reestablished and the pressure responsive member returns to the initial or rest position with zero deflection. Pressure measurements can subsequently be made from the reference transducer. These measured pressures are $p_2$, but since $p_1 = p_2$, they are equivalent to measuring $p_1$.

Because the deflection of the pressure responsive member is held substantially near zero with the foregoing apparatus, the elasticity of the pressure responsive member becomes a substantially non-critical factor in the operation of the invention, unlike the prior art devices which rely on the deflection of the member for pressure measurements. Another advantage of the present invention is that its sensitivity can be adjusted simply by increasing the loop gain. Calibration of the transducer 116 is unnecessary with the present invention and the system 100 itself can be calibrated as needed or desired just as any other instrument. Zero checks of the apparatus can be made at any desired time. Yet another advantage of the present invention is that it is simpler to construct the transducer itself since the returning light signal does not need to be linear or of any particular magnitude because the system 100 does not directly rely upon the measurements of the returned light signal to provide a pressure measurement. Finally, since the returning light signal does not need to be linear, no linearization software is necessary with the present system because the system is always as linear as the reference transducer.

The present invention having thus been described, other modifications, alterations, or substitutions may now suggest themselves to those skilled in the art, all of which are within the spirit and scope of the present invention. For example, if desired, a pressure relief valve may be incorporated in the pressure variation means to allow air to be drawn into the pressure chamber 108 so as to account for air leakage from the system. Additionally, either a single fiber may be used or a fiber bundle may be used in lieu of the two fiber system shown herein. Where a single fiber is used, it will serve as both the transmission and return paths. Furthermore, while the present invention has been described with reference to zeroing the transducer to a $\Delta p = 0$ condition, that is, a zero deflection of the pressure responsive member, it will be understood that the system could as readily be constructed for a transducer zeroing condition of $\Delta p = c$, where c is equal to a predetermined constant and the pressure responsive member is deflected a pre-established amount. It is therefore intended that the present invention be limited only by the scope of the attached claims below.

I claim:

1. A closed loop pressure determination system incorporating a pressure transducer comprising:

a lumen enclosing an optical pathway having proximal and distal ends for sending and receiving light signals, said lumen including a sealed internal passage;

said pressure transducer comprising a pressure responsive member disposed at said distal end of said optical pathway, said member having first and second surfaces wherein said first surface is exposed to a first variable pressure $p_1$ sought to be repeatedly determined, said member second surface being pressure coupled to said passage at a second variable pressure $p_2$, said pressure responsive member being provided for modulating a light signal traveling along said optical pathway in response to changes in said first variable pressure $p_1$;

a reference pressure sensor, said reference pressure sensor being pressure coupled to said lumen passage, said reference pressure sensor providing an output signal indicative of said pressure $p_2$;

a comparator in signal receiving communication with said pressure transducer for receiving said modulated light signal and in communication with a signal source indicative of a pre-established reference pressure $p_{ref}$, and for providing a comparator output signal indicative of the pressure difference $\Delta p$ wherein $$\Delta p = p_{ref} - (p_1 - p_2);$$

and a pressure variation means connected to said comparator for receiving said output signal, said lumen passage being sealingly connected in fluid flow communication with said pressure variation means, said means being provided for varying the pressure $p_2$ within the passage and on the second surface in response to the comparator output signal so as to make $p_2 = p_1 + c$, where c equals a predetermined constant.

2. The system of claim 1 wherein said optical pathway is disposed within said sealed internal passage of said lumen and comprises a single fiber optic transmission path for sending light signals to said pressure transducer and a single fiber optic return path connected between said pressure transducer and said comparator for returning said modulated light signal to the comparator.

3. The system of claim 1 wherein:

said optical pathway comprises at least one optically conducting elongate fiber;

said pressure transducer comprises a cylindrical housing defined by a cylindrical wall having an aperture in one side of the cylindrical wall and an internal bore receiving said distal end of said optical pathway in a predetermined position relative to said aperture; and said pressure responsive member is disposed on said housing in covering relation to said aperture and is free to deflect in response to changes in said pressures $p_1$ and $p_2$, said first surface of said member being directed outward relative to said aperture and said second surface of said member being directed inward relative to said aperture.

4. The system of claim 3 wherein said pressure responsive member comprises a sleeve encircling said housing.

5. The system of claim 1 wherein said pressure variation means comprises an audio speaker coil having means to generate air pressure changes in a pressure chamber connected to said lumen passage.

6. A method of determining a pressure $p_1$ using a closed loop control apparatus, said apparatus including:

a pressure transducer, said pressure transducer including:

a lumen enclosing an optical pathway having proximal and distal ends, said lumen including a sealed internal passage;

a pressure responsive member disposed at said distal end of said optical pathway, said member having first and second surfaces wherein said first surface is exposed to a first variable pressure $p_1$ sought to be repeatedly determined, said member second surface being pressure coupled to said passage at a second variable pressure $p_2$, said pressure responsive member being provided for modulating the intensity of a light signal traveling along said optical pathway in response to changes in said first variable pressure $p_1$;

a reference pressure sensor means, said reference pressure sensor means being pressure coupled to said lumen passage, said reference pressure sensor providing an output signal indicative of said pressure $p_2$;

a comparator for receiving said modulated light signal, said modulated light signal indicative of the pressure difference $p_1-p_2$ between the first and second surfaces, and a signal indicative of a preestablished reference pressure $p_{ref}$ and for providing a comparator output signal indicative of the pressure difference $\Delta p$ wherein $$\Delta p = p_{ref} - (p_1 - p_2);$$

and a pressure variation means for varying the pressure $p_2$ within the lumen passage;

wherein said method comprises:

establishing a fixed reference pressure signal independent of said reference pressure sensor means for a condition where $p_1+c=p_2$, where c equals a predetermined constant;

generating a modulated light signal by operation of said pressure responsive member;

providing said modulated light signal and said reference pressure signal to said comparator;

comparing said modulated light signal and said reference pressure signal;

providing a comparator output signal to said pressure variation means, said comparator output signal indicative of the difference between said signal indicative of said reference pressure and said modulated light signal;

varying the pressure $p_2$ by said pressure variation means within the passage and on the second surface in response to the comparator output signal so as to make $p_2=p_1$; and determining the pressure $p_2$ and therefore the pressure $p_1$ with said reference pressure sensor.

7. The method of claim 6 wherein said reference pressure signal is established to be indicative of a zero pressure differential across said pressure responsive member and the constant c=0.

* * * * *

UNITED STATES PATENT AND TRADEMARK OFFICE
CERTIFICATE OF CORRECTION

PATENT NO. : 5,517,998
DATED : 05/21/96
INVENTOR(S) : Dennis S. Madison

It is certified that error appears in the above-indentified patent and that said Letters Patent is hereby corrected as shown below:

col. 5, line 5, delete "coveting" and insert --covering-- therefor.

Signed and Sealed this

Twenty-ninth Day of April, 1997

Attest:

BRUCE LEHMAN

Attesting Officer

Commissioner of Patents and Trademarks